United States Patent
Price et al.

(10) Patent No.: US 6,280,759 B1
(45) Date of Patent: *Aug. 28, 2001

(54) METHOD OF CONTROLLED RELEASE AND CONTROLLED RELEASE MICROSTRUCTURES

(76) Inventors: Ronald R. Price, 114 Monopanson Dr., Stevensville, MD (US) 21666; Joel M. Schnur, 6009 Lincolnwood Ct., Burke, VA (US) 22015; Paul E. Schoen, 5006 Taney Ave., Alexandria, VA (US) 22304; Mary Testoff, 7746 Mandan Rd., Greenbelt, MD (US) 20770; Jacque H. Georger, Jr., 8409 Great Lake La., Springfield, VA (US) 22153; Alan Rudolph, 3447 Everette Dr., Bowie, MD (US) 20716; Robert F. Brady, 706 Hope La., Gaithersburg, MD (US) 20878

( * ) Notice: Subject to any disclaimer, the term of this patent is extended or adjusted under 35 U.S.C. 154(b) by 0 days.

This patent is subject to a terminal disclaimer.

(21) Appl. No.: 08/206,149

(22) Filed: Mar. 7, 1994

Related U.S. Application Data

(62) Division of application No. 08/077,503, filed on Jun. 17, 1993, now Pat. No. 5,492,696, which is a continuation of application No. 07/668,772, filed on Mar. 11, 1991, now abandoned, which is a continuation-in-part of application No. 07/343,762, filed on Apr. 14, 1989, now Pat. No. 5,049,382.

(51) Int. Cl.$^7$ .................................................. A01N 25/28
(52) U.S. Cl. ...................... 424/408; 424/411; 424/499; 424/417; 424/418; 424/419; 424/405; 424/406; 424/420; 523/122
(58) Field of Search ..................................... 424/404, 408, 424/411, 499, 450, 420, 417, 418, 419, 406, 405; 264/4.4, 4.7; 523/122; 106/15.05

(56) References Cited

U.S. PATENT DOCUMENTS

| | | | |
|---|---|---|---|
| 2,791,202 | * | 5/1957 | Doyle .................................... 424/411 |
| 3,826,232 | * | 7/1974 | Duffey et al. ......................... 119/157 |
| 4,244,836 | * | 1/1981 | Prensch et al. ....................... 252/316 |
| 4,469,613 | * | 9/1984 | Munteanu et al. ..................... 252/92 |
| 4,849,223 | * | 7/1989 | Pratt et al. ............................ 424/409 |
| 4,911,981 | * | 3/1990 | Schnur et al. .................... 428/402.24 |
| 5,049,382 | * | 9/1991 | Price et al. ............................ 424/450 |
| 5,416,205 | * | 5/1995 | della Valle et al. .................... 514/54 |

FOREIGN PATENT DOCUMENTS

| | | | | |
|---|---|---|---|---|
| 0168862 | * | 1/1986 | (EP) | ..................................... 424/412 |
| 1190969 | * | 5/1970 | (GB) | ................................... 424/411 |

OTHER PUBLICATIONS

Insect Suppression with Controlled Release Phenomona Systems Kydonieus et al.ed. CRC Press 1982 pp 200–204.*

* cited by examiner

Primary Examiner—Neil S. Levy
(74) Attorney, Agent, or Firm—Oblon, Spivak, McClelland, Maier & Neustadt, P.C.

(57) ABSTRACT

Tubules which contain an active agent in their lumen and compositions containing such microtubules are effective for providing a slow, controlled release of the active agent. Such microtubules are useful in the production of coating compositions for the protection of surfaces coming into contact with water, adhesive resins for the production of laminated wood products, and devices for dispensing pesticides.

14 Claims, 5 Drawing Sheets

METHOD OF CONTROLLED RELEASE AND CONTROLLED RELEASE MICROSTRUCTURES

This is a division, of application Ser. No. 08/077,503, filed on Jun. 17, 1993 now U.S. Pat. No. 5,492,696, which was a continuation of application Ser. No. 07/668,772, filed on Mar. 11, 1991, now abandoned, which was a continuation-in-part of application Ser. No. 07/343,762, filed on Apr. 14, 1989, now U.S. Pat. No. 5,049,382.

BACKGROUND OF THE INVENTION

1. Field of the Invention

The present invention relates to a method of controlled release of an active ingredient or agent, microstructures for the controlled release of an active ingredient or agent, and compositions containing such microstructures. In particular, the present method relates to the use of submicron diameter hollow cylinders (tubules) which contain an active agent within the inner hole or lumen of the tubule for the controlled release of the active agent. The tubules may be self-assembled from lipids or peptides or other self-assembly molecules and may be coated with electroplated metal or ceramics. Alternatively, the tubules may be constructed of an inorganic material such as a metal or ceramic.

2. Discussion of the Background

As man constructs artifacts, nature, in the form of weather, microbes and marine life, works to break the artifact down and return it to nature. Since before recorded history, man has applied coatings to artifacts to both beautify and protect the artifact.

Coatings incorporating materials which are aimed at destroying or diverting microbes and marine life are known. The most common coatings are paints used on land based structures of all types and marine coatings used on seaside and seaborne artifacts such as pilings, ship hulls, towers and other structures.

Biological fouling of surfaces such as ship hulls exposed to seawater is a problem which has existed since man first put to the sea. The diversity of fouling organisms and the environments in which they live create complex problems which any useful antifouling coating must overcome. Because these organisms add weight and hydrodynamic drag when they attach to vessels, effective hull fouling control is necessary to minimize fuel consumption, maintain operational speed and maneuverability, and preserve the hull from corrosion.

The schemes to defeat the attachment of drag producing organisms to ships and other man made artifacts almost matches the diversity of the organisms themselves. Any useful biocidal system must be effective against organisms which range from slime-forming bacteria and algae to shell-forming invertebrates with minimal damage to the remainder of the environment.

By definition, biocidal agents are highly toxic to the target species and to other animals and plants as well. The use of highly toxic and environmentally persistent antifoulants such as lead, mercury, arsenic, and cadmium compounds has been discontinued because of environmental degradation. In addition, the highly effective tributyltin compounds have also been banned from use by several state and federal agencies as well as foreign governments because of the detrimental overall impact.

Although in use in one form or another for over a thousand years, the predominant toxicant in use today is copper in the form of copper sulfate, copper hydroxide, cuprous oxide, copper napthenate or copper metal in powder or sheet form. Too great a concentration of copper can also be harmful to the environment. Paints and coatings in use today contain up to 70% by weight of cuprous oxide and release to the environment far more than the minimum effective amount of copper. Of course, the rate of copper release declines exponentially as the coating ages because exposure of the paint to the environment leaches active toxins until the paint is no longer effective.

Although now the toxin of choice, copper is an environmental hazard which is toxic to invertebrate and vertebrate marine organisms which include many economically valuable species such as oysters and clams, fish and seaweed. The release of copper to the environment must be carefully controlled. In addition, if large quantities are inhaled or ingested during hull repainting, copper oxide can be a hazard for dockyard workers. In contained waters which are frequented by large ocean-going vessels, such as the Suez Canal, the water quality has deteriorated because of high levels of copper. Paints which release high levels of copper may soon be restricted by environmental regulation.

Many inventors have tried to find a way of balancing the beneficial against the detrimental effects of releasing copper or other agents to prevent microbial or marine fouler action adjacent a treated surface. U.S. Pat. No. 4,098,610 describes a biocidal glass additive for marine paints which slowly releases copper. U.S. Pat. No. 4,129,610 describes a water soluble coating for ships which slowly releases copper. Another slow toxin release scheme is described by Foscante et al. in U.S. Pat. No. 4,385,134, in which a polymer is used as the slow release agent. Other marine anti-fouling paints and coatings are described in U.S. Pat. Nos. 4,480,011; 4,594,365; 4,602,011. U.S. Pat. No. 4,531,975 describes a marine coating which uses hollow glass bead microspheres or balloons to thicken and change the coating's density.

The mechanisms and history of antifouling paints as well as a discussion of the problems with ablative or erodible type dispensing coatings can be found in U.S. Pat. No. 4,670,481 to Foscante et al. Foscante describes a paint incorporating tributyltin.

A deficiency of soft ablative paints and in some of the harder leaching paints is rapid mechanical erosion caused by flowing seawater. Often erosion of the coating in the bow, skegs, struts, and keel sections of the ship is more rapid than that in large flat surfaces. Paint is removed quickly from those areas, and the underlying hull is exposed to the ravages of marine fouling agents.

Coatings or paints which incorporate particles of copper or similar materials have the added problem that erosion of the ablative coating surrounding the particle can result in the sudden release of the particle and loss of its benefits. Thus without rational control of the leaching of toxicant from the coating, premature release of large amounts of the biocide in a dropped particle pollutes the environment and reduces the long term performance of marine antifouling paint. other problems are present when secondary or auxiliary toxins are used. Secondary toxin materials cannot be effective in promoting extended service lifetimes of conventional coatings unless these highly soluble materials can be protected from rapid leaching and chemical breakdown. Regardless of the myriad schemes developed to release copper and other toxins slowly, the problems of controlled slow release have not been solved.

The need for slow release of biocidal and pesticidal agents is not restricted to a marine environment. In many land environments, mold and other microbial and insect pests attack houses, vehicles and other land based artifacts. Copper and other toxic materials are incorporated into paints coatings and roofing material to suppress or destroy pest activity. U.S. Pat. Nos. 3,894,877; 3,888,683; 3,888,682; and 3,888,176 are all directed at incorporating algaicidal materials into roofing products. Land based artifacts suffer ablative wear similar to sea borne artifacts. A constant exposure of fresh toxic material is needed to protect the coated surface from microbial or pest infestation.

The attack of wood and laminated wood products, such as plywood, represents a particularly important case of biological degradation of man-made objects. specifically, larva of insects, such as carpenter ants, termites, powder post beetles, and wood boring bees, are known to attack wood and the resins which bind the individual sheets of wood in a section of plywood together ("Application of fenitrothion microcapsule for insect-proof plywood panel", M. Kawashima, T. Ohtsubo, S. Tsuda, T. Itoh, and K. Tsugi, *Proceedings of the 7th International Symposium on Microencarsulation and Controlled Release*, p. 88.) resulting in a weakening of the plywood. Further, insects such as termites and carpenter ants are well known to eat wood. The reduction in strength of the wood and plywood arising from the attack of such pests can jeopardize the structural integrity of a building and cause great economic loss.

Conventionally, plywood and lumber are pressure treated with agents such as creosote, cooper sulfate, arsenical compounds, organotin compounds. However, such conventional treatments are not satisfactory, because heavy metal compounds, arsenical compounds, creosote and organotins cause environmental degradation, are a health hazard to persons who handle and use woods, and are toxic in large amounts. Thus, it is desirable to provide methods and compositions for the slow, controlled release of agents which will afford protection to such wood products.

Another situation, where the slow, controlled release of a biologically active agent is desirable is the application of pesticides to agricultural crops. Such pesticides include not only insecticides and fungicides, but also selective herbicides for the control of weeds. Conventional methods for the controlled release of pesticides and herbicides include microencapsulation. However, such methods provide only a modest increase in the time of effectiveness (from 1–2 days to 5–7 days).

The slow, controlled release of pesticides is also important for the protection of animals, such as pets and farm animals. Thus, flea and tick collars are designed to release pesticides such as 2-chloro-1-(2,4,5-trichlorophenyl)vinyl dimethyl phosphate at a slow and controlled rate. However, conventional flea and tick collars have effective lifetimes which are only on the order of months, and the release of the agent is not linear with time. Thus, many animal owners are reminded that it is time to change an animal's collar, by discovering that the animal is infested with fleas or ticks.

In addition to providing methods and compositions for the slow, controlled release of pesticides, microbicides, herbicides, fungicides, insecticides, and bactericides, the slow, controlled release of beneficial agents such as fertilizers, trace nutrients, vitamins, hormones and the like is also desirable. Specific applications, include the application of fertilizers to agricultural crops, house plants and garden plants, shrubs, and trees. Conventional techniques for the controlled release of such agents suffer from the same drawbacks as described above, e.g., short increase in the time of effectiveness and/or nonlinear release with time.

It is known that materials may be incorporated and released in a linear manner, or on demand. Many types of encapsulation in spherical particles, or in solid rods have been well established (D. Wise, *Biopolymeric Controlled Release Systems*, Vol. II, CRC Press, Boca Raton, (1984).

As described in U.S. Pat. No. 3,318,697, it is known to metal coat lipid and wax globules. For pharmaceutical and other purposes, it is known to incorporate materials inside a waxy globule or a liposome.

It is further known that polymerizable phospholipids form hollow cylindrical structures which are commonly referred to as tubules. These are described in U.S. Pat. Nos. 4,877,501 and 4,990,291. The efficient synthesis of these compounds is fully described in U.S. Pat. No. 4,867,917 entitled "Method for Synthesis of Diacetylenic Compounds". The methods necessary to coat these microstructures with a range of metals is fully described in U.S. Pat. No. 4,911,981 entitled "Metal Clad Lipid Microstructures".

These tubules are hollow tube-shaped microstructures fabricated by self organization of polymerizable diacetylenic phospholipid molecules. Morphologically, tubules are analogous to soda straws with diameters of approximately 0.05 to 0.7 $\mu$m and lengths from 1 to 1,000 $\mu$m. The tubule diameter, the length and the number of bilayers comprising the wall are all controllable parameters which are controlled by the fabrication methods employed.

The preparation of tubules is also discussed in an article by Schnur et al., "Lipid-based Tubule Microstructures", *Thin Solid Films,* 152, pp. 181–206, (1987) and the articles cited therein. That same article, in which one of the inventors is a co-author, also describes metal coating tubules and using them as microvials to entrap, transport and deliver polymeric reagents to a desired site. However, there is no suggestion of using such tubules for controlled release of an active agent.

Burke et al, ("Entrapment of 6-Carboxyfluorescein within Cylindrical Phospholipid Microstructures", Thomas G. Burke, Alok Singh, Paul Yager, *Annals of the New York Academy of Sciences. Biological Approaches to the Controlled Delivery of Drugs*, Ed. R. L. Juliano, 507, 330–333 (1987)) disclose the entrapment of the hydrophilic fluorophore, 6-carboxyfluorescein, in the lumens of such tubules. The movement of liposomes within the tubule is reported. Again, there is no suggestion of utilizing such tubules for the slow, controlled release of an active agent.

Each of the ablative or erodible materials of the prior art tend to dispense particles of material to the environment which causes an uneven and sometimes overly high concentrations of the toxic material. In addition, the agent to be dispensed often reduces or weakens the integrity of the coating. Thus, there remains a need for methods and compositions for the slow, controlled release of active agents.

SUMMARY OF THE INVENTION

Accordingly, it is one object of the present invention to provide methods and compositions for the controlled, slow release of an active agent.

It is another object of the present invention to provide methods and compositions for the long term release of an active agent with a zero order or first order release rate.

It is another object of the present invention to provide an antimicrobial, algaicidal, herbicidal, and pesticidal (generically referred to as biocidal) coatings and devices which will slowly dispense a biocidal material to the environment adjacent to the coating or device.

It is another object of the present invention to provide a biocidal coating in which the toxic material strengthens the coating.

It is another object of the present invention to provide a method of and coating compositions for protecting a surface from biological fouling on contact with water, in particular sea water.

It is another object of the present invention to provide a method of and a coating composition for dispensing controlled amounts of a metal (such as nickel, cobalt, gold, palladium, and copper) or an alloy (such as Ni—B, Ni—P, Ni—Fe—B, Co—B, and Co—P) to the environment at an acceptable rate to meet industry and regulatory agency standards.

It is another object of the present invention to provide a method of and a coating for dispensing controlled amounts of other secondary or additional biocidal materials together with copper.

It is another object of the present invention to provide a method of and a coating composition for the controlled slow release of toxic agents.

It is another object of the present invention to provide a method of and compositions for protecting wood and laminated wood products, such as plywood, particle board, fiber board, wafer board, and macroscopic wood composites such as beams, arches, etc. from decay resulting from attack by fungi, bacteria, insects and morine borers.

It is another object of the present invention to provide a method of and compositions for the controlled slow release of fertilizers.

It is another object of the present invention to provide a method of and compositions for the controlled, slow release of pesticides.

It is another object of the present invention to provide a method and devices for the long-term protection of animals from insects and arachnids, such as fleas and ticks.

These and additional objects of the invention, which will become apparent in the course of the following detailed description, have been achieved by the inventors' discovery that tubules, which contain an active agent within the lumen of the tubule, are effective for providing a slow, controlled release of the active agent to the environment surrounding the tubule.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
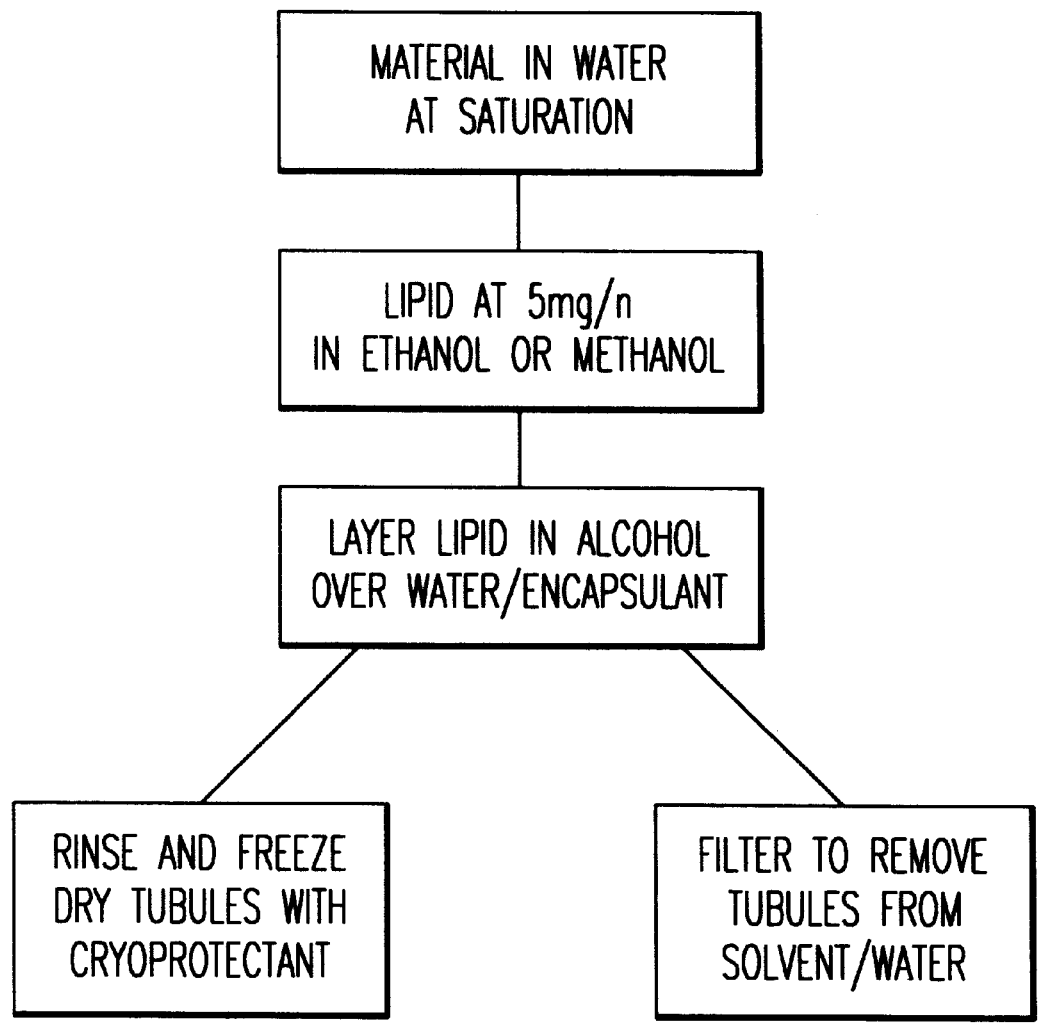
FIG. 1 illustrates a flow diagram showing the steps for encapsulation of materials within the bilayer walls of lipid tubules.
Figure 2:
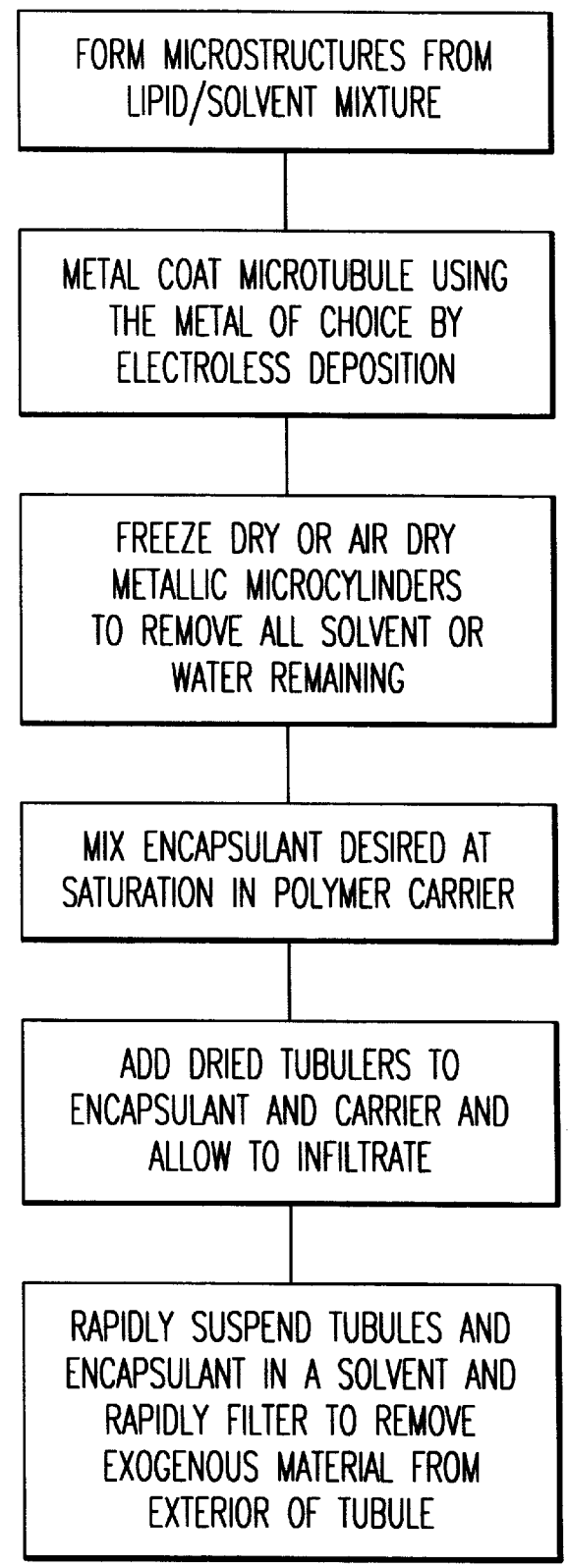
FIG. 2 illustrates a flow diagram showing the steps for encapsulation of materials within the core of metal clad microstructures.

Accordingly, the present invention relates to tubules which contain an active agent in the lumen thereof and a method of effecting the controlled release of an active agent to an environment by treating the environment with such tubules or a composition containing such tubules. Preferably, the lumen of the tubule contains a carrier in addition to said active agent.

Essential to the production of microstructures containing an active agent for controlled release is the utilization of methods necessary to ensure efficient capture of the agents which are to be released.

In the practice of this invention the capture of the agents to be delivered may be accomplished by capillary action into the central core of the cylindrical microstructures. The central core of metal clad microstructures varies from 0.2 to 0.35 microns. For non-metal coated tubules the interior diameters average 0.4 microns.

Tubules may be either air or freeze dried to provide hollow micro-capillary spaces. Encapsulation of the agent is accomplished by mixing the desired agent with a carrier whose viscosity is sufficient to ensure that the capillary forces acting on the carrier will allow it to be retained during processing. This carrier may be a high viscosity monomer, a linear polymer or a polymerizable crosslinking material. At distances greater than 100 nm the method of retention for encapsulant materials is capillary action, and within 100 nm of the interior surface the retention is dominated by surface adsorption and adhesion of the encapsulant.

The release rate for a given agent is determined by the diameter of the inner space, by the viscosity of the carrier, by the relative solubilities of the agent in the carrier and in the surrounding matrix, and molecular weight of the active agents as well as that of the carrier. The nature of the external matrix in cases where these structures are included in coatings, composites or solvents also effects the leachate rate. By suitably controlling these parameters linear release rates can be achieved from periods of minutes to years.

Removal of the exogenous agent is accomplished by suspending the microstructures/encapsulant in a large volume of solvent and rapid filtration of the microstructures. Alternatively, in the case of a metallized tubule, metal tubule, or tubule which is otherwise stable to plasma etching, the exogenous encapsulant may be removed by spreading a thin film of the tubule mixture, and exposing that film to a plasma etch to remove the excess agent, leaving the material in the interior of the tubule in place due to the protection afforded by the metal overcoat of the microstructures.

The resultant microcylinders with contained agent may then be stored dry in a powder form, or may be stored suspended in a liquid which is a non-solvent for the encapsulated material.

Agents may be encapsulated in the hollow core of lipid microstructures by methods similar to the above. Several limitations exist on materials and methods used to encapsulate materials into lipid tubules. Lipid microstructures are not stable at temperatures in excess of their chain melting transition temperatures, nor are they resistant to being solubilized in alcoholic or hydrocarbon based solvents, or resistant to typical plasma etches, therefore any technique must address the need to maintain microtubule structure during processing, storage and use. Following formation and during subsequent processing steps such as lyophilization (freeze-drying) of the microtubules, materials used as viscosity increasers, or active encapsulant must not be solvents for the lipid. The agent is loaded in the tubules by capillary attraction and retained by both capillary forces and surface adsorption. Exogenous agent is more difficult to remove as the tubules are not mechanically resistant to removal techniques. Prolonged exposure to the agent is not desirable.

A further means of incorporating an active agent in the lumen may be achieved by capture during the self-assembly of microstructures. This is achieved by forming the microtubules at the interface of a solvent and water, in which the solvent is methanol or ethanol in which the lipid is dissolved, and an underlayer of water in which the encapsulant material is dissolved. The encapsulant is retained between the bilayers which comprise the wall of the microstructures.

Tubules

As noted above, suitable tubules include those prepared as described in U.S. Pat. Nos. 4,877,501, 4,911,981, and 4,990,291, which are incorporated herein by reference. Thus, the present tubules include those prepared by the self organization of polymerizable diacetylenic phospholipid molecules and those obtained by the metallization of such tubules.

Alternatively, the tubule may be any tubule of the appropriate dimensions prepared from a suitable material. Metal tubules may be prepared by plating a metal on a filament which is soluble in a hydrocarbon solvent, to form an outer layer of metal, and then removing the central filament by exposure to a hydrocarbon solvent. Alternatively, a porous membrane may be plated with a metal to form a layer of metal on the inside surface of the pores, dissolution of the membrane, and collection of the metal tubules.

A critical aspect of the tubules is, of course, the dimension of lumen. Suitable inner diameters for the present tubule range from 0.05 to about 20 $\mu$m, preferably from 0.1 to 1 $\mu$m, most preferably from 0.2 to 0.8 $\mu$m. As noted above, the inner diameter of the tubules may be controlled, by selection of the conditions used to produce the tubules.

The most preferred inner diameter will depend on the choice of active agent, carrier, environment surrounding the tubule, other components of the composition (if the tubules are present in a composition), and the desired time period of release. Generally, the diameter of the lumen will be 2 to 1,000 times the average diameter of the active agent, preferably 20 to 500 times the average diameter of the active agent.

Although the present tubules are not limited to those of any specific length, it is to be understood that for any given tubule the time of effectiveness will increase with an increase in the length of the tubule. Generally, the tubules will be of a length ranging from 1 $\mu$m to 1 mm, more typically from 10 $\mu$m to 200 $\mu$m.

Active Agents

Suitable active agents include: herbicides, pesticides, antibiotics, antihelmetics, antifouling compounds, dyes, enzymes, peptides, bacterial spores, fungi, hormones, etc.

Examples of suitable herbicides include:
Tri-Chloro Compounds (Triox, Ergerol)
Isothiazoline (C9211)
Chlorothanolil (Tuffcide).

Examples of suitable pesticides include:
Malathion
Spectricide
Rotenone.

Examples of suitable antibiotics include:
Albacilin
Amforol
Amoxicillin
Ampicillin
Amprol
Anaprime
Aureomycin
Aziumycin
Chlortetracycline
Oxytetracycline
Gallimycin
Fulvicin
Garacin
Gentocin
Liquamicin
Lincomix
Nitrofurizone
Penicillin
Sulfamethazine
Sulfapyridine
Fulfaquinoxaline
Fulfathiazole
Sulkamycin.

Examples of suitable antihelmetics include:
Ivermictin
Vetisulid
Trichlorofon
Tribrissen
Tramisol
Topazone
Telmin
Furox
Dichlorovos
Anthecide
Anaprime
Acepromazine
Pyrantel Tartrate
Trichlofon
Fabentel
Benzimidazoles
Oxibenzidole Examples of suitable antifouling agents include:
Ergerol
Triazine
Decanolactone
Angelicalactone
Galactilone
Any Lactone Compound
Capsicum oil
Copper Sulphate
Isothiazalone
Organochlorine Compounds
Organotin Compounds
Tetracyclines
Calcium Ionophores such as 504, C23187
Tetracycline Examples of suitable hormones include:

Estrogen
Progestin
Testosterone
Human Growth Factor

Carriers

The selection of the carrier is determined by the viscosity of the carrier and the solubility of the active agent in the carrier. The carrier must possess a sufficiently low viscosity so that it can fill the lumen of the tubule as a result of capillary action.

If the agent is soluble or is mobile in the carrier, then the rate of release depends on the diffusion rate and solubility of the agent in the carrier and in the external matrix (if present). If the agent is insoluble or immobile in the carrier, then the rate of release depends on the rate of release of the carrier itself from the tubule.

In the present context, release can mean delivery of the agent to a surrounding matrix (e.g., in a coating composition), to an environment in which the agent is soluble (e.g., water) or to a gaseous environment (e.g., the atmosphere when the agent is volatile).

Accordingly, suitable carriers include low molecular weight polymers and monomers. Specific examples of such polymers include:
Polysaccharides
Polyesters
Polyamides
Nylons
Polypeptides
Polyurethanes
Polyethylenes
Polypropylenes
Polyvinylchlorides
Polystyrenes
Polyphenols
Polyvinyl pyrollidone
Polyvinyl alcohol
ethylcellulose
gar gum
polyvinyl formal resin
water soluble epoxy resins
Quietol 651/nma/ddsa
Aquon/ddsa/nsa
urea-formaldehyde
polylysine
chitosan
polyvinyl acetate and copolymers and blends thereof Specific examples of such monomers and monomer mixtures include:
quietol (dimethyl-amino-dimethyl-isovaleryl-propyl-ester-hydrobromide)
aquon
(meth)acrylates (e.g., $C_{1-4}$-alkyl (meth)acrylates),
diacids with diamines
polyols with polyisocyanates
ethylenically unsaturated compounds
diols with diacids
diols with glycidyl compounds Thus, the molecular weight of the carrier can range from low values (carrier is a monomer) to high values (carrier is a polymer). In general, for any given tubule and agent, the rate of release of the agent will decrease as the molecular weight of the carrier increases.

The present invention will now be discussed in terms of some particularly preferred embodiments.

Coating Compositions

A controlled rate of release of a toxicant from the surface of a coating can be achieved by creating a porous structure of controlled dimensions within a coating. The toxicant must migrate through the coating to reach the outer environment. This structure can be created by adding to a coating vehicle an effective amount of between five and seventy percent of the present tubules which contain or are composed of a biocidal toxicant.

The composition of the coating, and hence its characteristic rate of ablation, can be controlled by the concentration and type of the binder resins in the coating, the composition and type of the ablative resin or filler, if any, and the relative hardness of the coating. The rate of release of the toxicant as a function of area of applied coat can be further controlled by the loading of the tubules in the vehicle, the concentration of toxicant contained in the tubules, the dimensions of the tubules (material diffuses into the environment through a gradient), and solubility modifiers within the encapsulated co-toxicant. The biocidal toxicant is chosen during the manufacture of the tubules, and its rate of release can be further modified during encapsulation by the addition of solubility modifiers such as glues, resins, polymers and other "slow release agents".

The tubules can be metallized with any metal capable of being plated. It is preferred that the tubules be made of copper, but nickel may be used in some applications. The copper as well as other metals can be in pure form or can be alloyed such as copper with zinc or other metals to improve or enhance the toxicity.

The preferred size of the tubules are from 1 to 1000 microns in length and from 0.05 to 1 micron in diameter. These microcylinders can be of any source of manufacture but it is preferred that these tubules be metallized lipid tubules because such tubules can be consistently formed to uniform dimensions in the desired size range.

Hollow tubules are formed from diacetylinic phosphatidylcholine by several different techniques such as heating the lipid above the phase transition temperature and then slow cooling the lipid to form the tubules. Alternatively, the tubules can be formed by heating the lipid above the phase transition temperature, rapidly cooling the lipid to about 0° C., raising the temperature above the phase transition temperature a second time and slowly cooling it to room temperature.

Preparation of starting materials and tubules is described in detail in several articles published by personnel of the Naval Research Laboratory (NRL). These procedures, which are incorporated herein by reference, are summarized and described in the article by Schnur et al., Lipid-Based Tubule Microstructures, Thin Solid Films, 152, pp. 181–206 (1987) at pp. 183–186.

Tubules are delicate and can be easily destroyed. It has been found that these tubules act as an excellent template which can be uniformly and continuously coated with metal either on one surface or, more preferably, on both surfaces. The most preferred metallization technique is electroless plating described in detail in the above referenced Schnur et al. article at pp. 198–200. The metal coating on the metallized tubules is of uniform thickness of about 20 nm both inside and outside the hollow tubule. The preferred coating is between about 20 nm and 2000 nm.

Once coated with metal, the tubules are filtered to remove the solvent and are air dried to a powder form. At this point the tubules can be stirred into the coating vehicle by gentle agitation. If the tubules are processed to a wet stage and then solvent exchanged with a coating compatible solvent, the tubules can be mixed directly into the coating with the diluent solvent.

When exposed to an environment such as the ocean or atmosphere, natural chemical reactions will begin to interact with the copper coating on the tubule wearing away minute quantities of pure copper or converting the copper to oxides. Both copper and its oxides are toxic to target pests and are dispensed to the environment at a relatively predictable and uniform rate because of the uniformity of the metal coating. of course, the rate at which the copper or copper compound dissolves is controlled by the solubility rate in the environment. These rates are easily calculable once the environment is known (e.g., salt vs. fresh water).

The small copper or copper and zinc coated tubules are an excellent anti-microbial or pesticidal agent by themselves. The toxic potential of the tubules can be increased by incorporating a secondary or co-biocidal agent into the tubule. As noted by Schnur et al., the tubules can act as microvials. These tubules can be filled by a variety of techniques including capillary action.

In the preferred embodiments of the invention the tubules are filled with an antifouling and antimicrobial agent such as tetracycline. Many organisms create an environment attractive to free swimming marine larva. By creating an environment which is inhospitable to these organisms, fouling by free swimming larva is reduced or eliminated. The types of materials which can be incorporated into the tubules to create inhospitable environment are bactericides, herbicides, molluskicides, insecticides, pesticides all generically referred to as biocides.

The choice of carrier is important to ensure that the agent is not instantly discharged on contact with an aqueous environment. This can be accomplished by several methods. First, the chemical compounds used can be of limited solubility in water. Second, organic materials of low solubility, such as muscilagenous binders like fish glues (one example could be LePage fish glue), cellulose, polypeptide polymers, or inorganic materials such as ceramics or silanes can be used as binders. A further method is to dissolve the compound in a monomeric material which can be polymerized once in place in the tubule lumen, preferably of equal solubility to the ablative binder. The ideal solubility modifier has a rate of dissolution which would compliment that of the metallic coating and the ablative binder. Such polymers can be selected from epoxies such as the Dow Corning DER series of resins or the Shell Epon series of resins, an acrylate resin such as methyl or hydroxymethyl methacrylate, a urethane resin or the like. Some of the urethanes themselves have fungicidal or pesticidal properties which can add to the total effect of our invention.

Alternatively, it has been found that the paint medium can penetrate into the tubule. If the tubule is loaded with a cotoxicant material, the paint may soak into the end regions of the tubule and aid in controlling the access of water to the material.

Once cured in place, the co-toxicant will be incorporated into the paint in such a manner that it will ablate or dissolve at a controlled rate which provides an excellent slow toxin dispensing coating. Preferably the ablative or dissolution rate of the binder, metal coated tubule and filler will be substantially the same.

Tubules which have been electroless plated with a copper metal layer or other metals known to have antifouling properties can be dispersed in a wide variety of organic binders. Once the matrix material of the coating cure, the tubules form a trabecular network within the body of the coating. This network when left hollow acts as a capillary for seawater or rainwater. When filled, the pore size of the tubules and the solubility of the encapsulated secondary toxicants controls the release of included toxicants within the vehicle. Copper ions are released from the metallic coating of the tubules and diffuse through the channels to the surface of the coating.

The hardness and ablation rate of the coating, such as paint, is controlled by the selection of the resins used as the coating vehicle. Such as vinyl-rosin mixtures, acrylics, polyurethanes, and epoxies have been used successfully for this purpose. If some property of the coating can be made to respond to the local environment, such as barnacle basal plate intrusion into the coating body, then the actual release of toxicant is limited to such areas. In addition, by use of polypeptide coating binders, it is possible to use the actual release of protease by fouling organisms as the stimulus to expose subsurface tubules and initiate localized toxicant release.

Further control of the coating properties and the release rates of the toxicants can be controlled by the orientation and distribution of the tubules by two methods. First orientation can be accomplished by coating the surface in the presence of a magnetic or electrical field which creates a preferred orientation of the tubules to the coated surface, either parallel or normal. In addition, in coatings where the film thickness is less than the average tubule length, the tubules can be oriented parallel to the surface.

Because of the aspect ratio and size of the tubules, the tubules can further act to form, within the coating, a network which adds improved physical characteristics. At the least the tubules extend down into the surface so that they are anchored in place. This ability to form a composite structure within the coating reduces the amount of wasted copper that drops out of the coating rather than dissolving in place.

The present compositions may be applied to a surface by any conventional technique. Thus, the coating compositions may be applied by roller, brush, or spray over a suitable primer or barrier coating. The tubules are easily dispersed in paint vehicles and may be applied by means commonly used in the application of paint coatings. In addition, the tubules may be dried, and metal or metallized tubules can be oxidized. Such oxidized tubules can be charged and applied to an oppositely charged surface by conventional powder coating technology.

The tubules are effective antifouling agents in any organic binder. Such organic resins such as acrylics, epoxies, polyurethanes, vinyls, rosins or mixtures of these may be used. The most preferred coating compositions are acrylic copolymers, epoxies and vinyls.

Wood Treatment, Fertilizers and Animal Protection Devices

Tubules coated with either iron or copper may be added to a glue which is used in the production of laminated wood, this may be an alkaline phenol adhesive a melamine-urea, urea-formaldehyde, epoxy, polyvinyl-butryl, polyvinylchloride or other suitable adhesive compound. The use of encapsulated beetle dispersant pheromones such as gammadecanolactone, or active agents such as isothaizalones, chlorothanolil, or a suitable EPA approved organophosphorous insecticide may be encapsulated at saturation. As the tubules are both solvent resistant and heat resistant when metal coated they protect the encapsulant from the active agents in the glue, and unlike polymeric capsules are able to withstand both the heat and pressure of bonding.

In the area of controlled release of agricultural chemicals, it is known that water quality may be degraded by the runoff of excess agricultural chemicals, such as pesticides, herbicides, and fertilizers, as well as plant hormones or growth stimulants used. By using microtubules coated with iron, these chemicals may be applied in much lower amounts, due to the more efficient application afforded by controlled release. Smaller amounts released over time will not overload natural waterways. Because of the very small size of the microcylinders, their ease of dispersibility, and the fact that they may be applied by electrostatic applicators, microcylinders offer a means of reducing exposure of persons handling these chemicals, on loading, by reduction of content volatility caused by encapsulation; inhalation of noxious chemicals is reduced, as the microcylinders are effectively filtered by dust masks and filters. Further, the high length to diameter ratio (aspect ratio) microcylinders lodge in the structures of plants and provide direct protection. The iron is subject to environmental degradation, and the microcylinders break down to iron oxide in the soil in a short period of time.

For use in the distribution of insecticides on animals, a specific application would be the distribution of organic insecticides for control of fleas and/or ticks on animals. Unlike the typical flea collar commonly available, which uses the polymeric structure of the collar as the means to control the release of the insecticide, the use of a very high loading of tubules, acts as a reservoir of active agent and offers prolonged linear release of the insecticide, at a safe and effective level over time.

It is to be understood that the present method and compositions include the use of mixtures of tubules containing different carriers and/or agents. In this case, the tubules containing the different agents (carriers) may have different dimensions. Thus, the release rate may be optimized for each agent within the same composition.

Having described the invention, the following examples are given to illustrate specific applications of the invention including the best mode now known to perform the invention. These specific examples are not intended to limit the scope of the invention described in this application.

EXAMPLES

Example 1

Unpolymerized tubules were produced from a mixed solvent system of 70% ethanol and 30% water by volume, with a lipid concentration of 2.5 mg/ml. The microtubules are formed at 27° C. and following formation are dialyzed against water at pH 1.0 in 0.1N HCL. A commercial palladium and tin catalyst (Shipley Co., Waterbury, Mass.) is used as received. Cuposit (Shipley Co., Waterbury, Mass.) a commercial electroless copper plating bath is used per the manufacturers instructions to copper plate the accelerated microtubules. Following the plating reaction the excess bath is removed and the tubules are filtered to remove excess water.

A commercial freeze drying apparatus is used to dry the metallized microtubules to a powder. The desired active agent at saturation in the selected carrier is added slowly to the dry microstructures during which time the material is captured by the microstructures by capillary attraction.

Exogenous material is removed by suspending the tubules in an excess of solvent and is followed by rapid filtration. These microstructures can again be dried or suspended in a diluent liquid.

Example 2

A dispersion of tubules was prepared as above, except that no metal plating was added to the surface of the microstructures. Following this, the tubules were dialyzed in a 50,000 molecular weight cutoff dialysis tube against distilled water to remove any lipid monomer and alcoholic solvent. The tubules were concentrated by filtration to remove excess water and were frozen in liquid nitrogen and dried on a commercial freeze drying apparatus.

The dry tubules were added to a mixture of the desired water soluble active agent at saturation in a hydrogel carrier at which time the tubules captured the material in the central core by capillary attraction.

Example 3

Lipid at a concentration of 2.5 mg/ml in ethanol is layered in a vertical cylindrical cylinder of glass which has a sufficient diameter to support an phase density separation between a water subphase and the ethanol/lipid superior phase. The desired active agent is added to the subphase of water. During formation of the microstructures at the alcohol/water interface, the agent is captured between the bilayers comprising the wall of the tubule.

The tubules are then either stored in a suitable liquid or are freeze-dried as in Example 2.

Example 4

Copper coated tubules were prepared as described in Example 1 and were mixed with a solution of polyethylene oxide in 1:1 water and ethanol. To this solution, 0.1 gr. of the water soluble fluorescent die, fluorescein, was added. The solution was then spun onto a silicon oxide wafer to form a thin film of the mixture. The film was dried by baking for one hour at 90° C. After drying, the wafer was then placed in an $O_2$ plasma etcher and etched for 10 minutes. The wafer was examined under an optical microscope before and after etching. Before etching, florescence could be seen throughout the field of the wafer, but after etching no fluorescence could be detected. Water drops placed in areas where tubule microstructures were present showed florescence in a matter of minutes demonstrating that the polyethylene oxide doped with fluorescein was encapsulated in metal tubules.

Example 5

Figure 3:
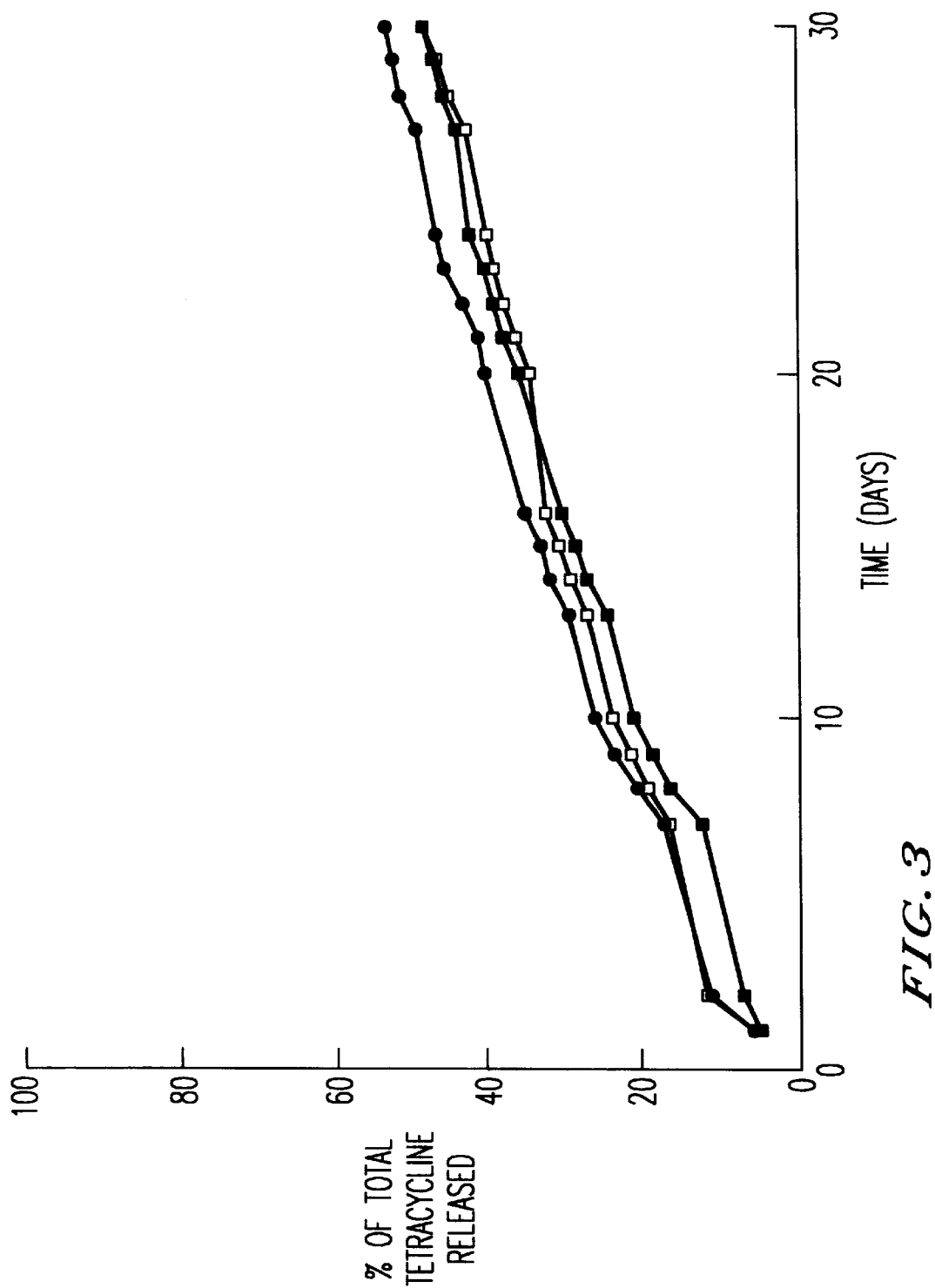
FIG. 3 illustrates the release of tetracycline from tubules containing epoxy monomer in the lumen.
Figure 4:
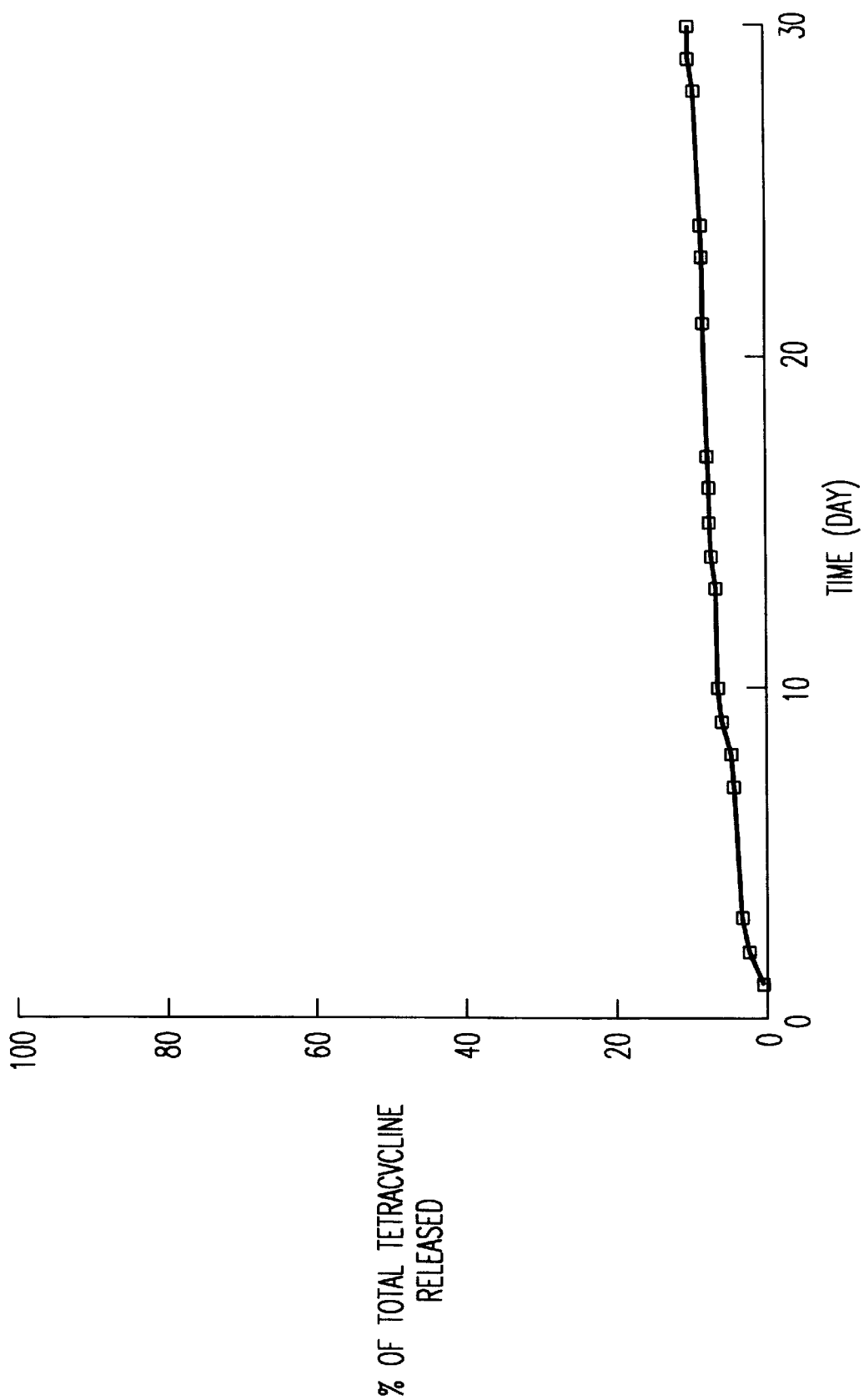
FIG. 4 illustrates the release of tetracycline from tubules containing epoxy polymer in the lumen.

Microcylinders of lipid are prepared as in Example 1, these cylinders contain oxytetracycline which is at saturation in an epoxy polymer (Quietol 651). FIGS. 3 and 4 illustrate controlled first order release from these tubules. FIG. 3 plots Q or the percent of total tetracycline released versus t or elapsed time. With the epoxy in monomeric form, the release over a thirty day period as measured by spectrophotometric absorption is observed in three trials to equal 50% of the total contained. FIG. 4 illustrates release from microstructures in which the epoxy is polymerized and when observed by the same procedure releases 10% of the encapsulated material over a thirty day period also in a linear manner. The above tubules were then added to a coating polymeric matrix of polyvinyl chloride and polyvinyl acetate resins and were coated onto a fiberglass rod. These rods along with controls of the base polymer and cuprous oxide powder (commercially available bottom paint from International Paint Company (Vinyl Lux™) were then exposed at Pearl Harbor, Hi. for a period of 180 days. The commercial paint after 180 days of exposure had over 50% coverage by hard fouling organisms, while the rods with tubules containing tetracycline did not exhibit significant fouling, after 9 months in water at Beaufort, N.C., test site. This coating was also tested for 90 days during the peak sediment season without hard fouling and has been tested in the Chesapeake Bay, Md., test site resulting in fouling-free surfaces.

Examples 6–10

The tubules are formed and metallized with electroless coating by methods described in U.S. Pat. No. 4,911,981. Once formed, the tubules are rinsed free from any residual lipid material or electroless plating bath chemicals in water. The tubules are then added to a saturated solution of the co-toxicant tetracycline and binder and allowed to dwell in this solution for a time sufficient to allow for the complete diffusion of the solution through the lumen of the tubule. Following this the tubules are allowed to settle out and the excess solution is removed. The tubules and the contained materials are allowed to dry and are then mixed into the coating prepared by mixing the following materials in the proportions by weight indicated.

Example 6

| | |
|---|---|
| Polyvinyl Resin (VYHH by Union Carbide) | 10% |
| Polyvinylbutryl Resin (Monsanto) | 5% |
| Polyvinyl Acetate Resin (Monsanto) | 1% |
| Methyl Isobutyl Ketone | 25% |
| Xylene | 30% |
| Copper Tubules Containing Tetracycline | 10% |
| Zinc Oxide (Fisher Scientific) | 9% |
| Molybdenum Disulphide (Climax) | 10% |

The vinyl resins are dissolved in the methyl isobutyl ketone and diluted with the xylene too form a solution of resin in solvent. The zinc oxide is added and followed by the addition of the tubules and molybdenum disulphide. This forms a Navy gray colored coating. The resulting mixture is painted onto primed steel panels for testing. Tests in the Chesapeake Bay showed that this coating provided inhibition of fouling.

Example 7

The coating composition is formed by mixing the following constituents in the proportions by weight indicated:

| | |
|---|---|
| Vinyl resin (e.g., VYHH by Union Carbide) | 55 |
| Rosin (e.g., R-307 by Fisher Scientific) | <200 |
| Tricresyl Phosphate, (e.g. T-342 by Fisher) | 50 |
| Methyl Isobutyl Ketone | 165 |
| Xylene | 115 |

To 970 parts by weight of the above mixture is added 61 to 150 parts by weight of copper tubules containing tetracycline. The mixture is stirred to wet and disperse the tubules and the resulting mixture is painted onto primed steel panels for testing. These panels were found to provide antifouling protection similar to those using cuprous oxide at a 70% by weight loading.

Example 8

Copper plated tubules containing tetracycline or Dowicide are added at a rate of 10 to 40 percent by weight to a copolymeric system such as acrylic or methacrylic ester monomers such as those described in U.S. Pat. No. 4,687,792 included herein by reference. This coating serves as a self ablative antifouling paint.

Example 9

Tubules containing a secondary toxicant material such as Tetracycline are incorporated into an epoxy resin vehicle as follows. Figures are in parts by weight

| | |
|---|---|
| Epoxy Resin (e.g., Shell Epon 828) | 60 |
| Versamid 140 (Henkel) | 40 |
| Zinc Oxide | 10 |
| Copper Tubules and Secondary Toxicant | 10 to 70 |
| Xylene | 150 |

The tubules are added to the Epon 828 along with the zinc oxide powder and dispersed. The mixture is diluted with the solvent and mixed with the versamid curing agent just prior to use. These coatings exhibit linear first order release of tetracycline in excess of 500 days.

Example 10

A coating is formed from a partly cured (tacky) epoxy or urethane resin which has been applied to the surface to be protected. To this tacky coating is applied a layer of copper coated tubules containing an active agent selected from the group consisting of antibiotics, herbicides, molluskicides, or pesticides suitable for use as antifouling toxicants. This layer is applied by blowing a dry powder preparation of the tubules containing the active agent onto the partly cured coating and allowing it to harden.

Examples 11 and 12

Testing of the following examples for antifouling formulations was accomplished as follows. The paints were brushed on test rods which were ¼" in diameter and 6" in length. These were suspended from a mesh of aquanet suspended from a float made of PVC pipe. The order of the rods in the array (Latin Square Array) is made such that in each row and column there are no repeated treatments. The arrays are suspended in the environment for a period of ninety days to nine months and are examined on a weekly basis, during which time the amount of settlement in percent is noted for each rod in each treatment. Rods which exhibit greater than 50% settlement are considered to have failed the test and are removed from the array. A statistical analysis is then made by species for each rod and for all controls. Each treatment series consists of a bare rod, the experimental coating, and the same base paint mix with active agent but without encapsulation in tubules. These arrays are located in Beaufort, N.C., Pearl Harbor, Hi., and LaTrappe Creek, Chesapeake Bay.

Example 11

Tubules were prepared as in Example 1. The active agent was either a chloroform extraction of the solitary coral species Renilla renillaformis commonly referred to as renillafoulin, or the commercially available C-11 analog of this compound gamma-decanalactone a pheromone which is non-toxic (irritant). This is added at saturation to quietol 651, a water soluble epoxy. The microcylinders are then added to a vinyl copolymer resin mixture in an organic solvent and applied to test rods of fiberglass. The following formulation is nominal for the material tested.

| | |
|---|---|
| VYHH Resin (Union Carbide) | 26.5 |
| VAGH Resin (Union Carbide) | 26.5 |
| Polyvinylbutryl Resin (Monsanto) | 1.0 |
| Methyl Isobutyl Ketone | 100 |
| Xylene | 250 |
| Copper Tubules Containing Renillafoulin or gammadecanalactone | 6 |

Figure 5:
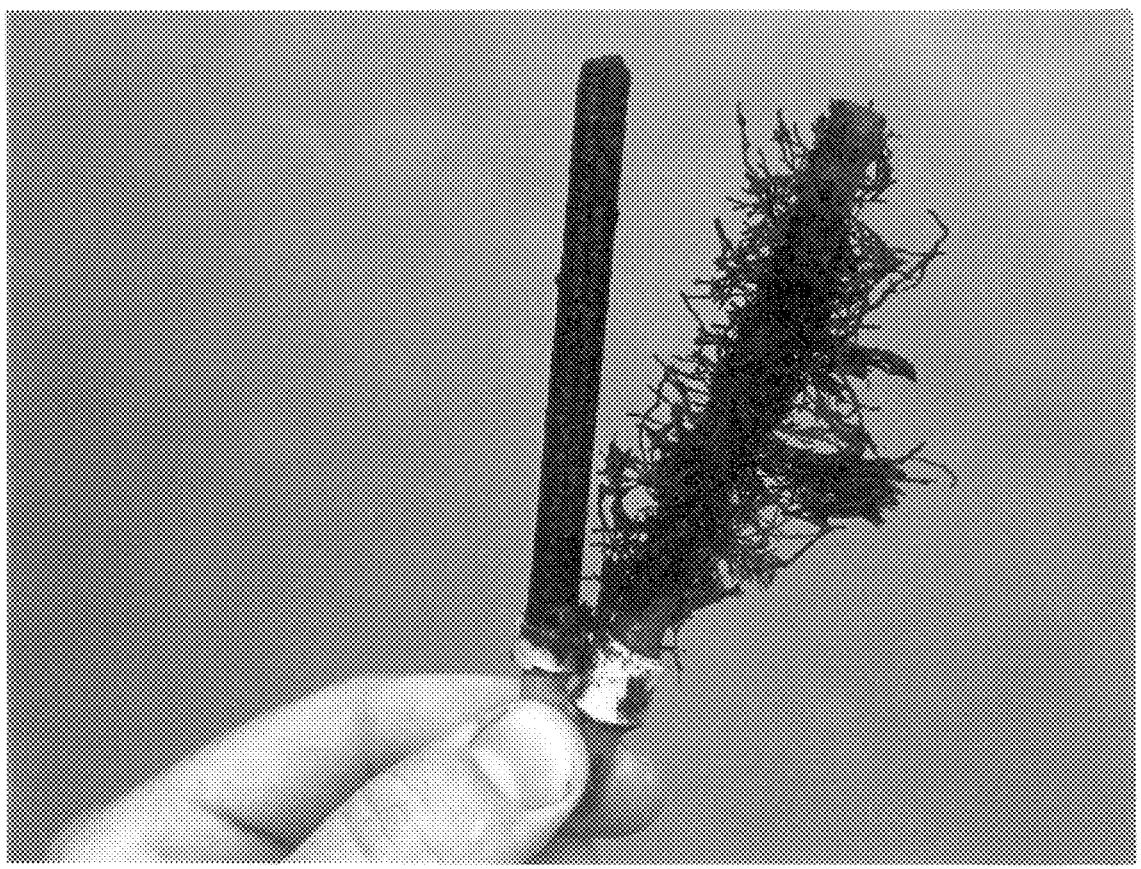

Following coating this mixture was applied to test array rods and tested in Pearl Harbor, Hawaii, Beaufort, N.C., and Chesapeake Bay, Md. Following exposures of test rod arrays in each area the results indicated that the rods would remain fouling free for the entire testing period unless there was a loss of surface adhesion with the test rod, or the coating had been mechanically abraded (See FIG. 5 in which the clean rod was treated as described and the fouled rod was treated with the base resin as described with no toxin or tubules).

Example 12

Microcylinders were prepared as in Example 1, and following this a mixture of isothiazolone (C9211 Rohm and Haas) was added to the tubules. The coating was prepared as in Example 11. Following testing the coatings were found to reduce or eliminate the formation of slime layers on the paint, but the coating was not 100% effective at repelling hard fouling species such as barnacles.

Preparation of Metal Tubules

1. Filaments of hydrocarbon solvent soluble polymer compounds of the proper diameters are activated by exposure to 0.1 M HCL at pH 1 for a period of one minute, following this step the filaments are exposed to a palladium tin catalyst for a period of ten minutes. Following this, the catalyst is activated by exposure to palladium chloride or tetrafluoroboric acid. Following this step a commercial plating bath is used to coat the polymer with metal. Copper, permalloy, or nickel boron is used to make a metal cylinder. Following the plating step, the polymer core is dissolved by hydrocarbon solvent leaving a hollow cylinder.

2. Using a polycarbonate membrane with small neutron track holes of the desired diameter, the membrane is exposed to HCL at pH 1, following this step the membrane is put into palladium-tin catalyst for two to 10 minutes. Following this step, the membranes are exposed to palladium chloride for a period of two minutes, then electroless plated with a commercial copper or nickel bath for ten minutes at room temperature. Removal of the membrane by chloroform or ethylene chloride, yields a surface from which tubules project. The tubules may be broken off the surface and collected for use.

The present invention provides an improvement over prior art in the use of the novel size and shape of the tubules to control: environmental degradation of materials; the attack of pests; and the delivery of beneficial agents, such as fertilizers. Also, the tubules form a short fiber reinforcement within a coating, and the metal coated tubules prevent the premature loss of large quantities of still active agents. In addition, the invention encapsulates and protects active agents, such as tetracycline, which would otherwise be removed from a coating by, e.g., water penetration, often prior to the desired time.

In addition to agents which are toxicants, the tubules can contain and distribute secondary agents such as anti-corrosion compounds or surface drag reduction agents. These improvements reduce the need for large quantities of metallic toxicants in antifouling coatings and lengthen the service life and operational flexibility of vessels or devices which utilize such coatings.

The present tubules may be utilized in many applications for the encapsulation and controlled delivery of a wide variety of agricultural chemicals, wood preservatives, paint additives, insecticides, anti-oxidants, enzymes, or biologically active compounds.

The present tubules when metallized are mechanically resistant and may be mixed with adhesives for inclusion in composite wood structures. If an active agent such as insecticides, fungicides or pesticides are used it renders the composite resistant to attack by insects, vermin or fungus and molds. Encapsulated agricultural chemicals such as herbicides, insecticides, nematocides, fungicides, mildewcides, growth hormones or stimulants may be applied once for prolonged action. If iron coated microstructures are used to encapsulate the active ingredients the microstructures may be mixed with a carrier diluent and disseminated by electrostatic applicators. Following environmental exposure the iron walls of the microcylinder oxidize and decompose into the environment.

Microtubules coated with metals exhibiting magnetic permeability such as Fe, Ni, Ni—B, Ni—P, Ni—Fe—B, and Co—B alloys may be loaded with enzymes or other active ingredients and added to chemical processes and then following the release of contents could be recovered by attraction to a magnet. In addition the microstructures may be manipulated by magnetic fields to be self agitating and therefore would aid in mixing encapsulated contents with the process chemistry.

Biologically active compounds may be delivered from microtubules. The advantage of microtubules over other delivery systems is that prolonged release may be obtained from these structures following injection through commonly employed hypodermic needles. Or they may be mixed with hydrogels and used in wound repair or as a medium for transdermal sustained drug delivery.

Obviously, many modifications and variations of the present invention are possible in light of the above teachings. It is therefore to be understood that, within the scope of the appended claims, the invention may be practiced otherwise than as specifically described.

What is claimed as new and desired to be secured by Letters Patent of the United States is:

1. A composition for effecting the controlled release of an active agent to an environment, comprising a tubule containing a solution or dispersion of an active agent in a carrier in the lumen thereof, wherein said tubule has an inner diameter of from 0.1 to 1 $\mu$m and a lenath of 1 $\mu$m to 1 mm.

2. The composition of claim 1, wherein said tubule is coated with metal.

3. The composition of claim 2, wherein said carrier is a polymer.

4. The composition of claim 1, wherein said active agent is one or more members selected from the group consisting of fungicides, herbicides, insecticides, pheromones, hormones, antibiotics, antihelmetics, and antifouling agents.

5. The composition of claim 1, wherein said tubule further comprises an additional amount of said active agent within the wall of the tubule or on the outside surface of the tubule.

6. The composition of claim 2, wherein said metal is copper.

7. The composition of claim 1, wherein said carrier is polyvinylchloride.

8. The composition of claim 1, wherein said carrier is a polysaccharide.

9. The composition of claim 1, wherein said carrier is a water soluble epoxy resin.

10. The composition of claim 1, wherein said active agent is tetracycline.

11. The composition of claim 1, wherein said active agent is tetracycline and said carrier is polyvinyl chloride.

12. The composition of claim 1, wherein said tubules consist of polymerizable diacetylenic phospholipid molecules.

13. A composition for effecting the controlled release of an active agent to an environment, comprising a tubule containing a solution or dispersion of an active agent in a carrier in the lumen thereof, wherein said tubule has an inner diameter of from 0.1 to 1 $\mu$m, and a length of 1 $\mu$m to 1 mm, and said active agent is selected from the group consisting of fungicides, herbicides, insecticides, pheromones, hormones, antibiotics, antihelmetics, antifoulants, and mixtures thereof and wherein said carrier is a polymer selected from the group consisting of polysaccharides, polyesters, polyamides, polypeptides, polyurethanes, polyethylenes, polypropylenes, polyvinylchlorides, polystyrenes, polyphenols, polyvinyl pyrrolidone, polyvinyl alcohol, polyvinyl formal resin, water soluble epoxy resins, urea-formaldehyde, polyvinyl acetate and mixtures thereof, and wherein said composition provides a zero order or first order release rate of said active agent from said tubule to said environment.

14. The composition as claimed in claim 13, wherein said active agent is selected from the group consisting of hormones, antibiotics and antihelmetics and wherein said carrier is a polysaccharide.

* * * * *